United States Patent
Loes et al.

(10) Patent No.: US 9,200,272 B2
(45) Date of Patent: Dec. 1, 2015

(54) EXTRACTION BUFFER AND METHOD FOR ISOLATING HIGH-QUALITY RNA FROM CELLS EXPOSED TO METAL CHLORIDE SOLUTIONS AND CLAY MINERAL SUSPENSIONS

(71) Applicants: Andrea Loes, Scottsdale, AZ (US); Shelley Haydel, Mesa, AZ (US)

(72) Inventors: Andrea Loes, Scottsdale, AZ (US); Shelley Haydel, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 30 days.

(21) Appl. No.: 14/197,489

(22) Filed: Mar. 5, 2014

(65) Prior Publication Data
US 2014/0256929 A1  Sep. 11, 2014

Related U.S. Application Data

(60) Provisional application No. 61/775,257, filed on Mar. 8, 2013.

(51) Int. Cl.
| | |
|---|---|
| *C07H 21/00* | (2006.01) |
| *C12N 15/10* | (2006.01) |
| *C07H 1/08* | (2006.01) |
| *C07H 1/06* | (2006.01) |
| *C07H 21/02* | (2006.01) |
| *C07H 21/04* | (2006.01) |
| *C07H 1/00* | (2006.01) |

(52) U.S. Cl.
CPC .............. *C12N 15/1006* (2013.01); *C07H 1/00* (2013.01); *C07H 1/06* (2013.01); *C07H 1/08* (2013.01); *C07H 21/02* (2013.01); *C07H 21/04* (2013.01)

(58) Field of Classification Search
None
See application file for complete search history.

(56) References Cited

PUBLICATIONS

Mills et al. Appl. Environ. Microbiol. (2004), vol. 70, pp. 5447-5458.*
Kim et al. Am. J. Physiol. Lung Cell Mol. Physiol. (2005), vol. 288, pp. L958-L965.*
Solymosy et al. European J. Biochem. (1968), vol. 5, pp. 520-527.*
Ando et al., Combined effects of manganese, iron, copper and dopamine on oxidative DNA damage, Journal of Health Science, 2011, vol. 57, No. 2, pp. 204-209.
Bag et al., Determination of Cu, Zn, Fe, Ni, and Cd by flame atomic absorption spectrophotometry after preconcentration by *Escherichia coli* immobilized on sepiolite, Talanta, 2000, vol. 51, pp. 1035-1043.
Bürgmann et al., mRNA extraction and reverse transcription-PCR protocol for detection of nifH gene expression by Azotobacter vinelandii in soil, Applied and Environmental Microbiology, Apr. 2003, vol. 69, No. 4, pp. 1928-1935.
Extracellular proteins and nucleic acids in soil, 19th World Congress of Soil Science, Aug. 1-6, 2010, Symposium 2.5.1.
Liang and Keeley, Detection of viable cryptosporidium parvurn in soil by reverse transcription-real-time PCR targeting hsp70 mRNA, Applied and Environmental Microbiology, Sep. 2011, vol. 77, No. 18, pp. 6476-6485.
Madrid and Camara, Biological substrates for metal preconcentration and speciation, Trends in Analytical Chemistry, 1997, vol. 16, No. 1, pp. 36-44.
Mangan et al., An effective method of RNA extraction from bacteria refractory to disruption, including mycobacteria, Nucleic Acids Research, 1997, vol. 25, No. 3, pp. 675-676.
Novinscak and Filion, Effect of soil clay content on RNA isolation and on detection and quantification of bacterial gene transcripts in soil by quantitative reverse transcription-PCR, Applied and Environmental Microbiology, 2011, vol. 77, No. 17, pp. 6249-6252.
Rajendhran and Gunasekaran, Strategies for accessing soil metagenome for desired applications, Biotechnology Advances, 2008, vol. 26, pp. 576-590.
Reno et al., Rapid isolation of total RNA from small samples of hypocellular, dense connective tissues, BioTechniques, Jun. 1997, vol. 22, No. 6, pp. 1082-1086.
Sanchez-Andrea et al., Microbial diversity in anaerobic sediments at Rio Tinto, a naturally acidic environment with a high heavy metal content, Applied and Environmental Microbiology, Sep. 2011, vol. 77, No. 17, pp. 6085-6093.
Zhao et al., An improved CTAB-Ammonium acetate method for total RNA isolation from cotton, Phytochemical Analysis, 2012, vol. 23, pp. 647-650.

* cited by examiner

*Primary Examiner* — Patrick Lewis
(74) *Attorney, Agent, or Firm* — Quarles & Brady LLP; Gavin J. Milczarek-Desai

(57) ABSTRACT

An RNA extraction buffer, an RNA extraction method, and an RNA extraction kit are described which enable functional, rapid, efficient, and high-quality RNA isolation from samples containing high concentrations of aqueous metal cations, clays, silica, or silicate minerals.

4 Claims, 3 Drawing Sheets

EXTRACTION BUFFER AND METHOD FOR ISOLATING HIGH-QUALITY RNA FROM CELLS EXPOSED TO METAL CHLORIDE SOLUTIONS AND CLAY MINERAL SUSPENSIONS

RELATED APPLICATIONS

This application claims priority to U.S. Provisional Application No. 61/775,257 filed on Mar. 8, 2013. The disclosure of this application is incorporated herein by reference in its entirety.

STATEMENT REGARDING FEDERALLY SPONSORED RESEARCH

This invention was made with government support under AT004690 awarded by the National Institute of Health. The government has certain rights in the invention.

BACKGROUND OF THE INVENTION

The isolation of RNA from biological samples is called RNA extraction. Such extraction from cellular material is complicated by the ubiquitous presence of ribonuclease enzymes in cells and tissues, which can rapidly degrade RNA. Methods commonly used in molecular biology to purify RNA from biological samples include guanidinium thiocyanate-phenol-chloroform extraction (phenol-chloroform extraction) and RNA extraction in liquid nitrogen.

The liquid-liquid extraction technique of phenol-chloroform extraction is widely used in molecular biology for purification of RNA. This method includes forming a biphasic mixture of equal volumes of a phenol:chloroform mixture and an aqueous sample. The method relies on phase separation by centrifugation of the phenol:chloroform mixture and the aqueous sample resulting in an upper aqueous phase and a lower organic phase. Extraneous cellular proteins partition in the organic phase while RNA partitions in the aqueous phase. RNA is subsequently recovered from the aqueous phase by precipitation with ethanol or 2-propanol. A disadvantage to phenol-chloroform extraction is that both phenol and chloroform are hazardous and inconvenient to use. Further, the extraction process is often laborious.

More difficulty lies in providing an extraction procedure that isolates RNA quickly in the presence of clays, phyllosilicates, or metal ions within the sample mixture. Most RNA isolation methods which remove metal ions from samples prior to extraction require lengthy wash steps prior to cell lysis which is undesirable for those who desire to perform metatranscriptomic and RNA analysis experiments.

The rapid isolation of RNA in the presence of metal cations is desirable as these cations can bind irreversibly causing RNA degradation. Additionally, through biosorption, living and non-living bacterial cells can pre-concentrate aqueous solutions of metal cations due to adsorption of metal ions to the chemical functional groups on the cell surface.

Thus, improvements in methods and systems for isolating RNA from bacterial samples exposed to clay mixtures, clay minerals, silicate minerals, including phyllosilicates, and aqueous solutions including metal cations are desirable.

SUMMARY OF THE INVENTION

The embodiments described herein relate to an RNA extraction buffer, method, and kit that can efficiently isolate total prokaryotic RNA from samples containing high concentrations of aqueous metal cations, clay, or silicate minerals. In one aspect, certain embodiments relate to an extraction buffer for isolating RNA including a sodium phosphate buffer with a pH of about 4.5 to about 6.0, about 1.0 M to about 2.0 M NaCl, about 0.2% hexadecyltrimethylammonium bromide (CTAB); and a chelating agent.

In an embodiment, a method is described for isolating RNA, including the steps of lysing at least one cell with an extraction buffer comprised of a sodium phosphate buffer with a pH of about 4.5 to about 6.0, about 1.0 M to about 2.0 M NaCl, about 0.2% hexadecyltrimethyl-ammonium bromide (CTAB), 1 mM 1,4-dithio-DL-threitol [DTT], and a chelating agent. The method further includes extracting isolated RNA from the lysis of at least one cell.

In an embodiment, a kit is described for isolating and extracting RNA from samples containing high concentrations of aqueous metal cations, clay, or silicate minerals. The RNA extraction kit includes an extraction buffer that is composed of a sodium phosphate buffer with a pH of about 4.5 to about 6.0, about 1.0 M to about 2.0 M NaCl, about 0.2% hexadecyltrimethylammonium bromide (CTAB), 1 mM 1,4-dithio-DL-threitol [DTT], and a chelating agent. The RNA extraction kit ideally further includes a spin column, a stock of DTT (to be rehydrated and stored at 4° C.), a wash buffer (with a notation to add X ml of 70% ethanol, whereby the final concentration of ethanol is 35%; e.g., the inventors have used an equal volume of 70% ethanol to arrive at a final concentration of 35% ethanol with Qiagen RNeasy columns), and RNase-free $H_2O$ for elution.

These and other aspects of the invention will be apparent upon reference to the following detailed description and figures. To that end, any patent and other documents cited herein are hereby incorporated by reference in their entirety.

DETAILED DESCRIPTION OF THE INVENTION

Figure 1:
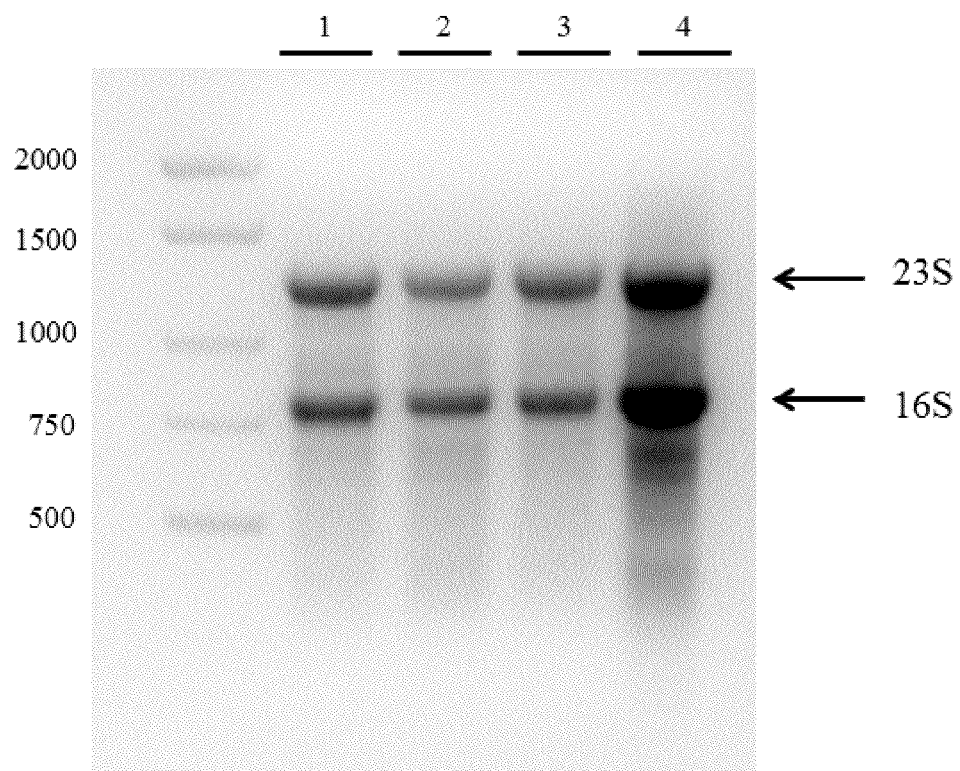
FIG. 1. Analysis of total RNA from *Escherichia coli* isolated by the developed extraction buffer and method. RNA was isolated from approximately $2.5 \times 10^9$ cells of *Escherichia coli* exposed for 15 min at 37° C. to (1) sterile, UV-irradiated, ultrapure, deionized $H_2O$ ($dH_2O$), (2) aqueous solution of transition metal chlorides prepared $dH_2O$ containing 200 μM $FeCl_3$, 80 μM $CuCl_2$, 40 μM $ZnCl_2$, and 4 μM $CoCl_2$, (3) and a 1% suspension of an antibacterial clay mixture (including silica and silicate, sulfide/sulfate, and feldspar minerals). RNA concentrations were determined spectrophotometrically (e.g., Nanodrop). Approximately 5 μg of sample was visualized by TAE agarose gel electrophoresis.

Embodiments described herein relate to an optimized protocol for the extraction of total RNA from bacterial samples exposed to clay mixtures, silicate mineral mixtures, or aqueous solutions of metal chlorides. The utilization of this method allows for the efficient extraction of ribonucleic acids from cell pellets containing high concentrations of aqueous transition metal chlorides as well as from clay mixtures and silicate mineral mixtures. This method has been demonstrated to yield approximately 80-200 µg of high quality RNA with limited genomic DNA contamination in less than ninety minutes from a pellet of *Escherichia coli* ATCC 25922 containing approximately 1×10$^9$ cells.

The purification of intact, high-quality microbial RNA from soil containing clay or silicate particles has been shown to be particularly problematic and difficult. This disclosure provides a method which can be used for the efficient extraction of intact microbial RNA from 2.5 g of an antibacterial clay mixture containing ~50% clay particles, ~50% silica, silicate minerals, sulfide/sulfate minerals, and feldspar minerals, and appreciable quantities of adsorbed metal cations, as well as directly from aqueous solutions of transition metal chlorides which have previously been shown to cause damage to nucleic acids.

The removal of metal cations from samples during RNA extraction without the addition of wash steps prior to cell lysis is a particular advantage for those desiring to perform transcriptional analysis on extracted RNA samples. This method could prove highly useful for those desiring to perform microarray analysis or RNA-Seq with cell samples exposed to high concentrations of aqueous metal cations.

Embodiments disclosed herein vastly improve the methods of RNA extraction. Also, it is important to note that extraction of intact, high-quality RNA can be performed in less than ninety minutes.

The extraction method is achieved by employing a novel extraction buffer including a pH of about pH 4.5 to about pH 6.0, preferably about 5.8 in order to minimize genomic DNA contamination. The extraction buffer further includes a concentration of NaCl from about 1 M to about 2 M. In an embodiment, the extraction buffer may include a concentration of NaCl of about 1.4 M.

This substantial increase in NaCl concentration limits the precipitation of hexadecyltrimethylammonium bromide (CTAB)-nucleic acid complexes during centrifugation at about 4° C. and incubation on ice (it is preferable to keep samples cold during RNA extraction to prevent degradation of the nucleic acids) and following addition of about 70% EtOH (CTAB has been shown to precipitate at concentrations of about <0.5 M NaCl). Additionally, to prevent precipitation of surfactant or high concentrations of salt with the nucleic acids, the column fractionation step of the RNeasy Total RNA Kit (Qiagen, Chatsworth, Calif., USA) was incorporated to collect the RNA.

NON-LIMITING EXAMPLES

Preparation of Extraction Buffer

A solution of 0.2% hexadecyltrimethylammonium bromide [CTAB], 0.2 M sodium phosphate buffer [pH 5.8], 1.4 M NaCl, 50 mM ethylenediaminetetraacetic acid [EDTA], was prepared and treated with 0.05% diethyl pyrocarbonate [DEPC]. After addition of DEPC, the solution was agitated for approximately 12 hours at room temperature, autoclaved (to inactivate the DEPC), and cooled to room temperature Immediately prior to use, 1,4-dithio-DL-threitol [DTT] was added to achieve a final concentration of 1 mM.

Bacterial Sample Preparation

An overnight culture of *Escherichia coli* ATCC 25922 was diluted 1:500 in fresh Luria Broth, grown with aeration at 37° C. to exponential phase (OD$_{600}$~0.3-0.6), and then diluted to OD$_{600}$=0.3. Aliquots of 12.5 mL were transferred to 15 mL conical tubes and harvested by centrifugation at 3500×g for 10 min at 4° C. Cell pellets were washed with 0.85% saline and resuspended in the appropriate experimental and control solutions: dH$_2$O; aqueous solution of transition metal chlorides prepared in dH$_2$O containing 200 µM FeCl$_3$, 80 µM CuCl$_2$, 40 µM ZnCl$_2$, and 4 µM CoCl$_2$; and 1% suspension of an antibacterial clay mixture (including silica and silicate, sulfide/sulfate, and feldspar minerals). Samples were then incubated for 15 min at 37° C. on a rotary drum, and cells were collected again by centrifugation at 3500×g for 10 min at 4° C.

RNA Extraction

Pellets from duplicate exposures were combined by resuspension in 1 mL of the developed extraction buffer and transferred to a screw-capped microcentrifuge tube containing ~0.5 mL of zirconium beads. Samples were processed in a Mini-Beadbeater (Biospec Products, Bartlesville, Okla.) at max speed for two 30-sec pulses, with ice incubations occurring in between pulses. Then, samples were centrifuged at 15,700×g for 2 min at 4° C. Supernatant was transferred to a new microcentrifuge tube and extracted with 1 mL chloroform-isoamyl alcohol (24:1) by rigorous shaking for approximately 30 sec, incubating at room temperature for 5 min, and then centrifuging at 10,000×g for 5 min at 4° C. Extraction with phenol-chloroform-isoamyl alcohol (25:24:1) would also be acceptable (followed by chloroform extractions). The aqueous phase was transferred to a new microcentrifuge tube and extraction was repeated twice with 750 µL chloroform-isoamyl alcohol (24:1). The aqueous phase was transferred to a new microcentrifuge tube and an equal volume of RNAse-free 70% EtOH was added. Sample was transferred to Qiagen RNeasy column and washed and eluted according to manufacturer's instructions. The RNA samples were stored at 70° C. RNA integrity was evaluated by electrophoresis through a 1.2% TAE agarose gel according to the method described by Masek et al. (2005).

Figure 2:
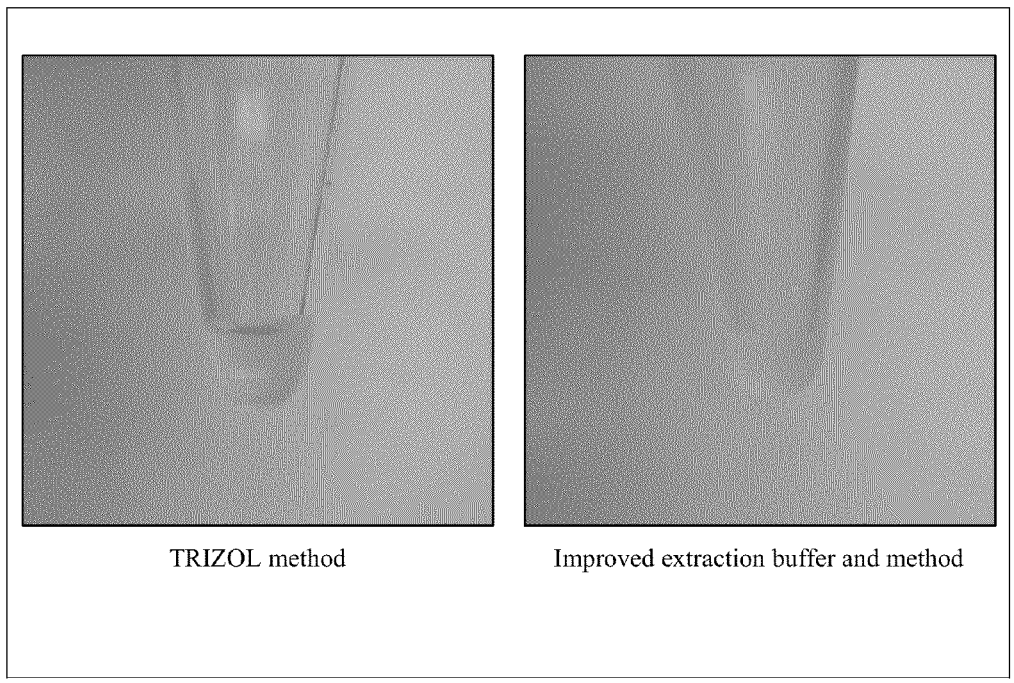
FIG. 2. Visual appearance of RNA samples following extraction using the $TRI_{ZOL}$® method and the developed extraction buffer and method. The removal of metal ions from RNA samples during extraction was visually assessed. These images represent the color of the RNA extracted by two different methods from *E. coli* exposed for 15 min at 37° C. to a solution containing 200 μM $FeCl_3$, 80 μM $CuCl_2$, 40 μM $ZnCl_2$, and 4 μM $CoCl_2$. Both samples were resuspended in $dH_2O$ following extraction. The inventors believe that the yellow color of the sample indicates that a higher concentration of ferric iron or other metal ions is present in the RNA sample extracted with $TRI_{ZOL}$® as compared to that extracted using our developed extraction buffer and method.
Figure 3:
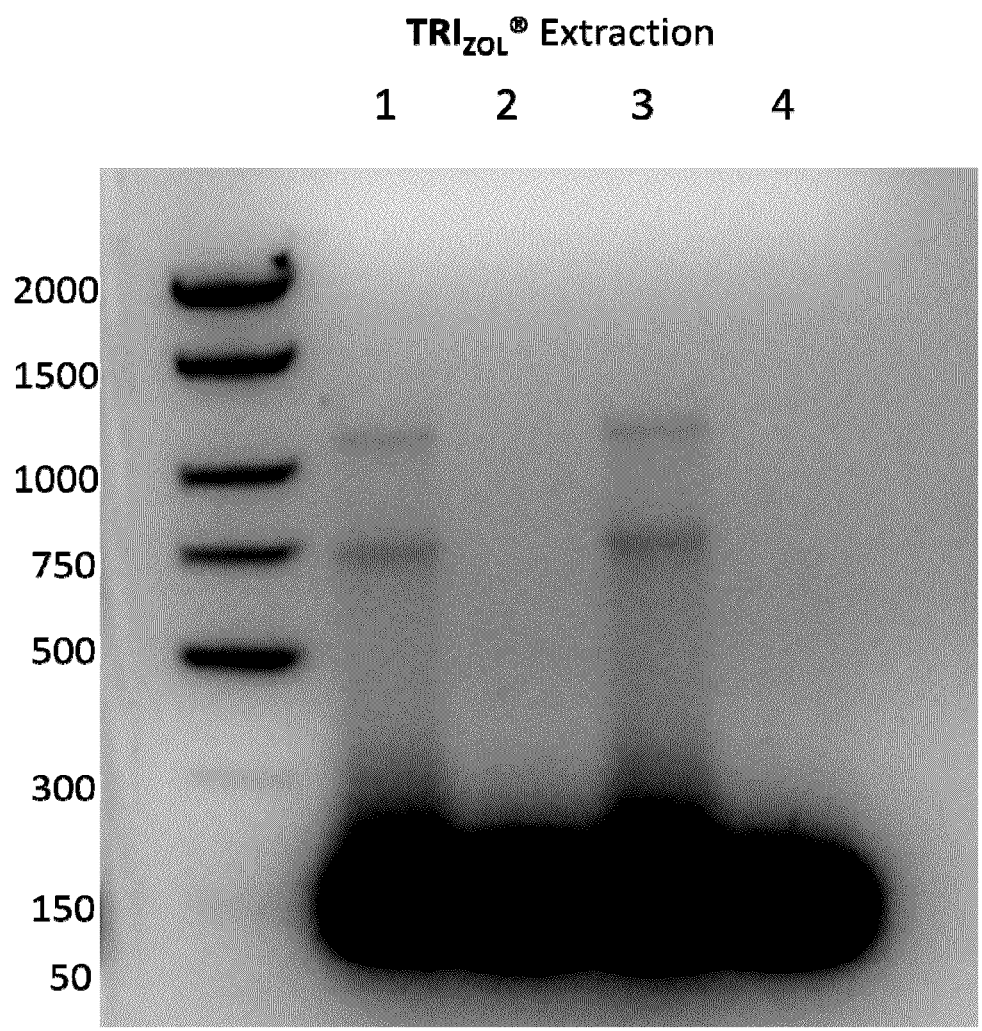
FIG. 3. Analysis of total RNA from *Escherichia coli* isolated using the $TRI_{ZOL}$® method. RNA extraction was performed in duplicate, and samples from each extraction are shown. Lanes 1 and 3: sterile, UV-irradiated, ultrapure, deionized $H_2O$ ($dH_2O$); lanes 2 and 4: aqueous solution of transition metal chlorides prepared in dH$_2$O containing 200 µM FeCl$_3$, 80 µM CuCl$_2$, 40 µM ZnCl$_2$, and 4 µM CoCl$_2$.

In preliminary studies, RNA extracted with TRI$_{ZOL}$® from *E. coli* exposed to aqueous metal chloride solutions showed degradation of the RNA. Additionally, we visually detected a bright yellow color in the extracted solutions, which the inventors believe indicated a persistence of ferric iron or other metals in the extracted RNA samples (FIG. 2). Extractions performed with the improved extraction buffer described herein yielded RNA pellets that appeared to retain significantly less metal cations than those extracted with the TRI$_{ZOL}$® method (FIG. 2). We visually assessed the RNA pellets to monitor the yellow color intensity of the extracted RNA. To quantify the concentrations of metal cations which remain in solution following extraction by these two methods, the extracted samples should be analyzed using inductively coupled plasma mass spectrometry.

Yields of intact RNA were particularly high. Even in samples containing high concentrations of transition metals, approximately 80-200 μg per $10^9$ cells of high quality RNA with limited genomic DNA contamination was consistently extracted.

The concentration of genomic DNA in samples extracted using this method is limited due to the low pH of the extraction buffer and the use of silica columns. However, if one wishes to proceed with experiments which require DNA removal, this procedure is highly adaptable to on-column DNA digestion protocols as columns are used to collect RNA sample.

The materials and methods described above are not intended to be limited to the embodiments and examples described herein.

The invention claimed is:

1. A method for isolating RNA from bacterial cells exposed to one or more of clay mixtures, clay minerals, silicate minerals, phyllosilicates, and aqueous solutions including metal cations, comprising the steps of:

lysing at least one of said bacterial cells; and extracting RNA separately from DNA with a mixture comprising a sodium phosphate buffer with a pH of about 4.5 to about 6.0, about 1.0 M to about 2.0 M NaCl, about 0.2% hexadecyltrimethylammonium bromide (CTAB), and a chelating agent.

2. The method of claim 1, wherein the NaCl concentration is about 1.4 M.

3. The method of claim 1, wherein the chelating agent is about 50 mM EDTA.

4. The method of claim 1, wherein the extracting step further comprises using said buffer further including about 0.05% diethyl pyrocarbonate for about 12 hours, with diethyl pyrocarbonate subsequently inactivated by autoclaving, and about 1 mM 1,4-dithio-DL-threitol added immediately prior to use.

* * * * *